US011617681B2

(12) United States Patent
Dennewill et al.

(10) Patent No.: US 11,617,681 B2
(45) Date of Patent: Apr. 4, 2023

(54) OPHTHALMIC IMPLANT SYSTEM FOR DRUG DELIVERY

(71) Applicants:SpyGlass Pharma, Inc., Aliso Viejo, CA (US); The Regents of the University of Colorado, a body corporate, Denver, CO (US)

(72) Inventors: James R. Dennewill, Aliso Viejo, CA (US); Malik Y. Kahook, Denver, CO (US); Glenn R. Sussman, Aliso Viejo, CA (US); Craig Alan Cable, II, Aliso Viejo, CA (US)

(73) Assignees: SpyGlass Pharma, Inc., Aliso Viejo, CA (US); The Regents of the University of Colorado, a body Corporate, Denver, CO (US)

( * ) Notice: Subject to any disclaimer, the term of this patent is extended or adjusted under 35 U.S.C. 154(b) by 0 days.

(21) Appl. No.: 17/839,956

(22) Filed: Jun. 14, 2022

(65) Prior Publication Data
US 2022/0339028 A1     Oct. 27, 2022

Related U.S. Application Data

(63) Continuation of application No. 16/893,372, filed on Jun. 4, 2020, now Pat. No. 11,399,977.

(51) Int. Cl.
*A61F 9/00* (2006.01)
*A61F 2/16* (2006.01)

(52) U.S. Cl.
CPC .......... *A61F 9/0017* (2013.01); *A61F 2/1662* (2013.01); *A61F 2002/1683* (2013.01);
(Continued)

(58) Field of Classification Search
CPC .... A61F 9/0017; A61F 2/1662; A61F 2/1613; A61F 2/1648; A61F 2002/16902; A61F 2002/1681; A61F 2/1694; A61F 2230/001; A61F 2230/0013; A61F 2250/0006; A61F 2250/0009; A61F 2250/0036; A61F 2250/0037; A61F 2250/0039;
(Continued)

(56) References Cited

U.S. PATENT DOCUMENTS 5,074,876 A   12/1991   Kelman
5,628,795 A   5/1997    Langerman
(Continued)

FOREIGN PATENT DOCUMENTS

EP   1543799 A1   6/2005
EP   3210572 A1   8/2017
(Continued)

OTHER PUBLICATIONS

Australian Examination Report for application No. 2020267203, dated Mar. 3, 2021, 3 pages.
(Continued)

*Primary Examiner* — Paul B Prebilic
(74) *Attorney, Agent, or Firm* — Polsinelli PC

(57) ABSTRACT

An ophthalmic implant configured for peri-operative, intra-operative, or post-operative assembly and disassembly. Drug delivery devices may be implanted with an intraocular lens, and later removed and replaced with new drug delivery devices.

14 Claims, 3 Drawing Sheets

(52) U.S. Cl.
CPC . *A61F 2230/0013* (2013.01); *A61F 2250/006* (2013.01); *A61F 2250/0067* (2013.01)

(58) Field of Classification Search
CPC ........ A61F 2250/006; A61F 2250/0067; A61F 2250/0068
See application file for complete search history.

(56) References Cited

U.S. PATENT DOCUMENTS

| | | | |
|---|---|---|---|
| 7,713,299 B2 | 5/2010 | Brady et al. | |
| 8,652,206 B2 | 2/2014 | Masket | |
| 8,663,235 B2 | 3/2014 | Tassignon | |
| 8,728,158 B2 | 5/2014 | Whitsett | |
| 9,358,103 B1 | 6/2016 | Wortz et al. | |
| 9,999,595 B2 | 6/2018 | Rakic et al. | |
| 11,399,977 B2* | 8/2022 | Dennewill | A61F 2/16 |
| 2003/0149479 A1 | 8/2003 | Snyder et al. | |
| 2006/0047339 A1 | 3/2006 | Brown | |
| 2007/0026042 A1 | 2/2007 | Narayanan | |
| 2007/0123981 A1 | 5/2007 | Tassignon | |
| 2008/0183289 A1 | 7/2008 | Werblin | |
| 2008/0200982 A1* | 8/2008 | Your | A61L 27/16 623/6.37 |
| 2009/0130176 A1 | 5/2009 | Bossy-Nobs et al. | |
| 2010/0204790 A1 | 8/2010 | Whitsett | |
| 2011/0125090 A1 | 5/2011 | Peyman | |
| 2011/0282328 A1 | 11/2011 | Ambati et al. | |
| 2011/0313521 A1 | 12/2011 | Angelopoulos | |
| 2012/0136322 A1 | 5/2012 | Alster et al. | |
| 2013/0190868 A1 | 7/2013 | Kahook et al. | |
| 2014/0148900 A1 | 5/2014 | Ratner et al. | |
| 2014/0288645 A1 | 9/2014 | Cuevas | |
| 2015/0209274 A1 | 7/2015 | Venkatraman et al. | |
| 2015/0238309 A1 | 8/2015 | Jansen | |
| 2015/0342729 A1 | 12/2015 | Kahook et al. | |
| 2016/0256262 A1 | 9/2016 | Wortz et al. | |
| 2016/0331519 A1 | 11/2016 | Kahook et al. | |
| 2017/0119521 A1 | 5/2017 | Kahook et al. | |
| 2017/0296331 A1 | 10/2017 | Werblin et al. | |
| 2018/0014928 A1 | 1/2018 | Kahook et al. | |
| 2018/0368974 A1 | 12/2018 | Kahook et al. | |
| 2020/0022840 A1 | 1/2020 | Kahook et al. | |

FOREIGN PATENT DOCUMENTS

| | | |
|---|---|---|
| KR | 10-2016-0045129 | 4/2016 |
| WO | 2008094518 A1 | 8/2008 |
| WO | 2008113043 A1 | 9/2008 |
| WO | 2016062503 A2 | 4/2016 |
| WO | 2018064578 A1 | 4/2018 |
| WO | 2018078026 A1 | 5/2018 |
| WO | 2018125930 A1 | 7/2018 |

OTHER PUBLICATIONS

Australian Examination Report for application No. 2020267203, dated Jan. 28, 2021, 8 pages.
Gonzalez-Chomon et al., "Drug-Eluting Intraocular Lenses", Materials 2011, 4, 1927-1940.
International Search Report and Written Opinion for PCT/US2021/035678, dated Aug. 28, 2021, 18 pages.
Liu et al., "Intraocular lens as a drug delivery reservoir", Curr Opin Ophthalmol 2013, 24:53-59.
Resul et al., "Structure-Activity Relationships and Receptor Profiles of Some Ocular Hypotensive Prostanoids", Survey of Ophthalmology, vol. 41, Supplement 2, Feb. 1997, S47-S52.
Stjernschantz, "From PGF 2a-Isopropyl Ester to Latanoprost: A Review of the Development of Xalatan the Proctor Lecture", Investigative Ophthalmology & Visual Science May 2001, vol. 42, 1134-1145.
Australian Government IP Australia, Decision to Grant, Patent No. 2020267203, dated Jul. 15, 2021, 28 pages.

* cited by examiner

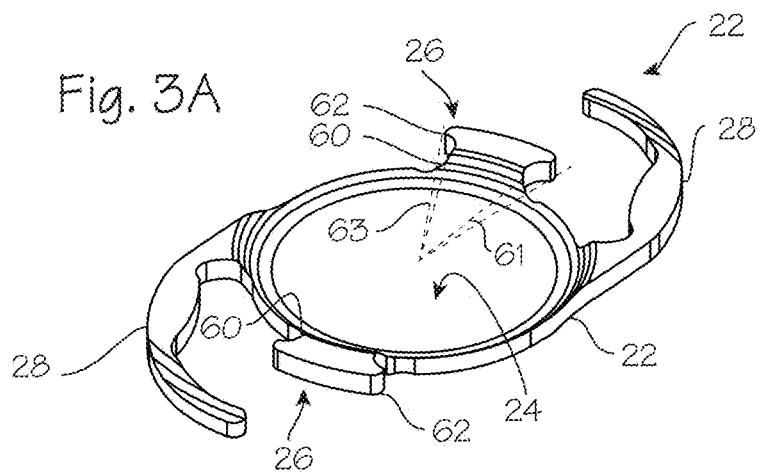
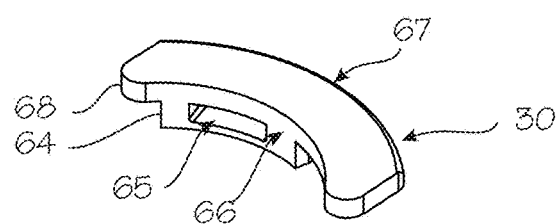
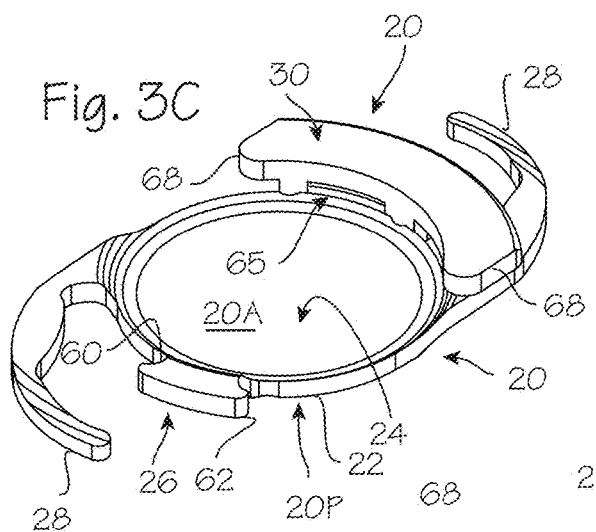
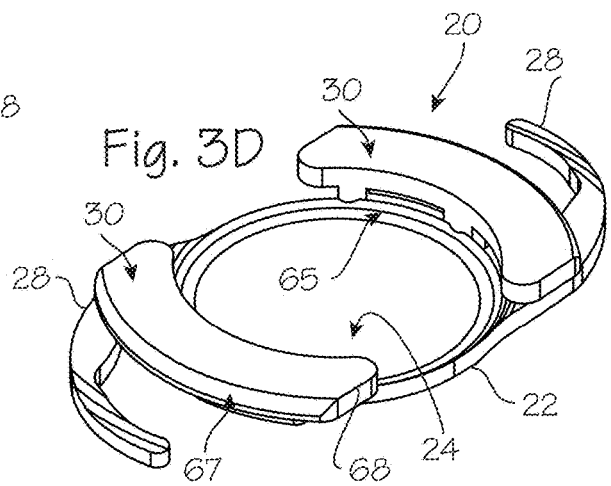

OPHTHALMIC IMPLANT SYSTEM FOR DRUG DELIVERY

RELATED APPLICATIONS

This application is a continuation of U.S. patent application Ser. No. 16/893,372, filed Jun. 4, 2020, now U.S. Pat. No. 11,399,977. This application is incorporated herein by reference in its entirety for all purposes.

FIELD

The inventions described below relate to the field of ophthalmic implants such as intraocular lenses.

BACKGROUND

Intraocular lenses (IOL's) are artificial lenses for the eye that can be implanted to replace the natural lens of a patient's eye after the natural lens is removed. The natural lens might be removed because it is affected by cataracts, and the IOL can be implanted to provide clear vision and some degree of focusing to the patient. Intraocular lens may also be implanted in a patient without removing the natural lens (a phakic intraocular lens or PIOL), to correct extreme near-sightedness or far-sightedness. It is advantageous to administer some therapeutic agents to the eye, coincident with implantation of the IOL, to alleviate various side effects of the IOL or treat other conditions of the eye that might coexist with the conditions that lead to cataracts. Side-effects such as infection and inflammation, and conditions such as glaucoma, can be treated with therapeutic agents that may be incorporated into additional devices that may be secured to the IOL. In addition to IOL's, ocular implants not including lenses may be implanted to address various other conditions. Kahook, et al., *Ophthalmic Device For Drug Delivery*, U.S. Pub. 20200022840 (Jan. 23, 2020) (the disclosure of which is hereby incorporated in its entirety) discloses various ophthalmic implant systems, including IOL systems including IOL assemblies combined with drug delivery devices.

SUMMARY

The devices and methods described below provide for easier placement of therapeutic agents along with ocular implants, including IOL's. This is accomplished with an ophthalmic implant system including a first or primary device, which may be an intraocular lens assembly or other intraocular implant, and a secondary device comprising a drug delivery device. The drug delivery device is configured for attachment to the intraocular lens assembly or other intraocular implant. Attachment of the drug delivery device to the intraocular lens assembly or other intraocular implant is accomplished through releasable or non-releasable means, and may be accomplished upon manufacture of the IOL assembly, peri-operatively immediately before or after implantation, or intra-operatively, in the same procedure in the IOL assembly is implanted. The drug delivery device may be configured to allow for placement of a second drug delivery component into the first drug delivery device, and placement may be may be accomplished upon manufacture of the IOL assembly, peri-operatively immediately before or after implantation, intra-operatively, in the same procedure in the IOL assembly is implanted. The first and/or second drug delivery device may be subject to depletion, and upon deletion may be removed and replaced, in an operation that may be accomplished long after the surgery in which the IOL assembly is first inserted.

BRIEF DESCRIPTION OF THE DRAWINGS

FIGS. 3A through 3D illustrate an ophthalmic implant system including an IOL assembly and a drug delivery device.

DETAILED DESCRIPTION

Figure 1:
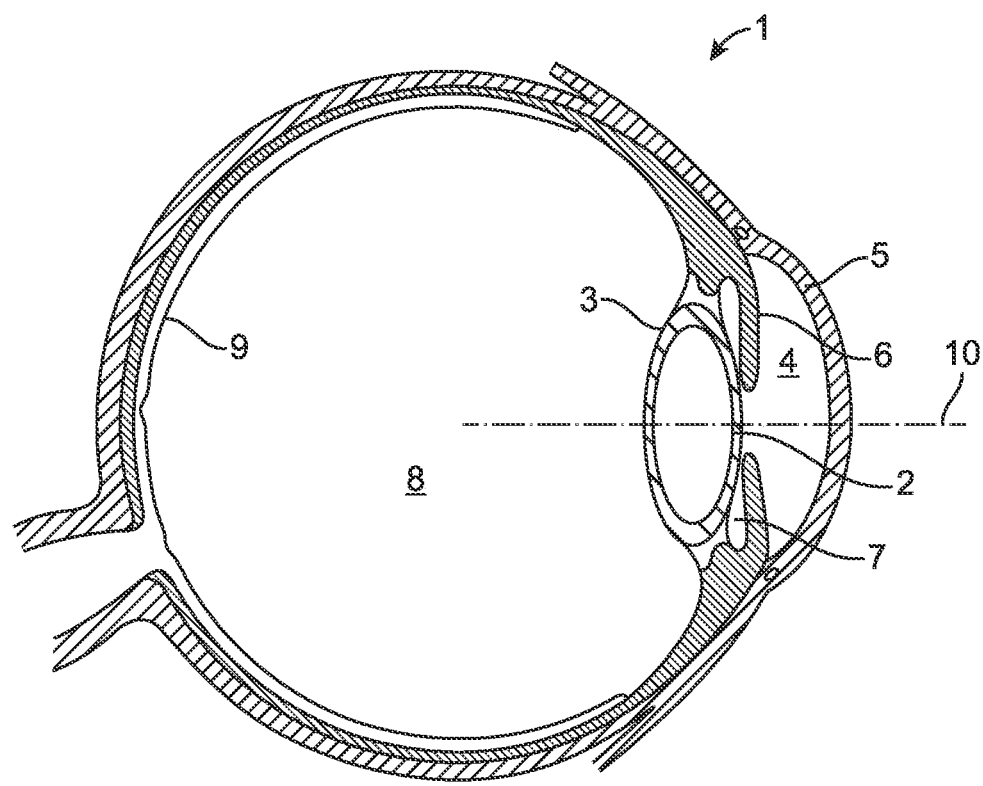
FIGS. 1 and 2 illustrate the environment of use of an ophthalmic implant system for drug delivery.
Figure 2:
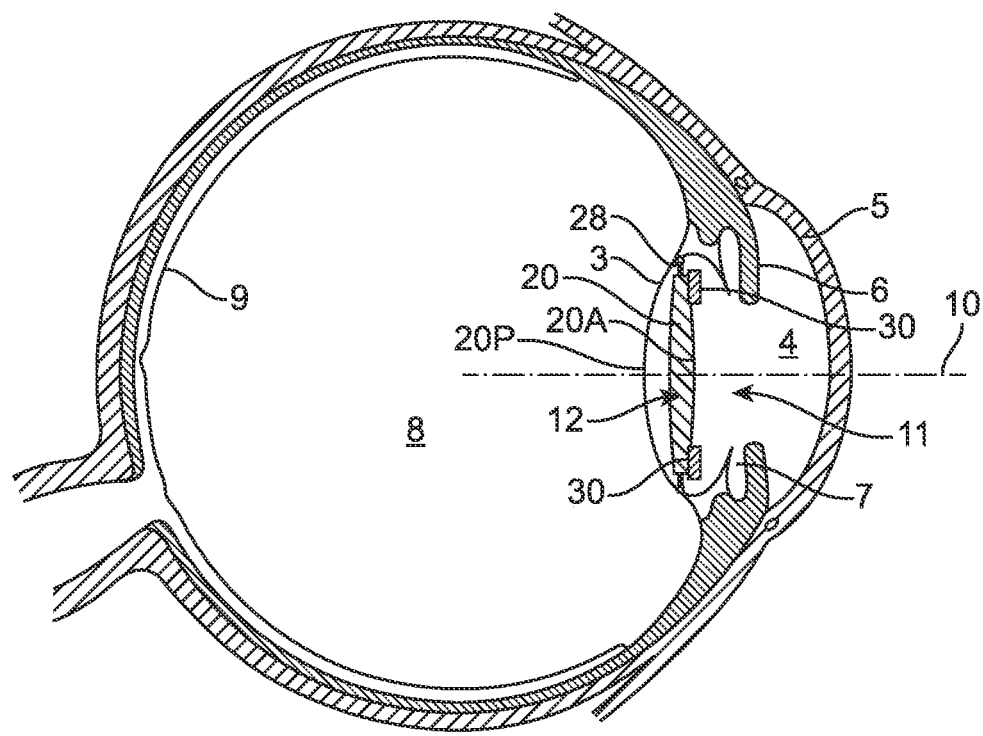

FIGS. 1 and 2 illustrate placement and use of an ophthalmic implant system in the eye of a patient. The eye 1 includes a lens 2 (the natural lens of the eye) and lens capsular bag 3, and the anterior chamber 4 which includes the cornea 5 and iris 6 and aqueous humour filling the space between the cornea and the iris, and a posterior chamber 7 between the iris and the capsular bag. The posterior cavity/vitreous body 8 is the large space between the lens and the retina 9. The natural lens 2 of the eye is characterized by an optical axis 10. (In the following description of the ophthalmic implant and or intraocular lens system, the terms posterior and anterior will be used in relation to the anatomy of the eye, in which the cornea is anterior and the retina is posterior.)

FIG. 2 illustrates a placement of the ophthalmic implant system or intraocular lens system 11 in the eye including the intraocular lens assembly 12 and drug delivery device 30 which is implanted in the capsular bag in conjunction with an intraocular lens assembly 12. As shown in FIG. 2, the drug delivery device is disposed anteriorly to the intraocular lens assembly 12, and is fitted over the intraocular lens assembly. The drug delivery device may also be placed below the iris and above the capsular bag. The capsular bag may contain the native lens, an artificial lens or no lens at all.

As shown in FIGS. 3A through 3D, a primary device is an ophthalmic implant system 20 which may include the IOL assembly 22, which includes a lens 24, one or more tabs 26 and one or more haptics 28, and one or more secondary devices 30. The ophthalmic implant 20 is characterized by an anterior surface 20A and a posterior surface 20P. In other embodiments the ophthalmic implant 20 may comprise other devices such as a capsular tension ring, or a capsular scaffold for holding the secondary device in place.

The secondary device 30 is a drug delivery device configured for attachment (preferably releasable attachment) to a tab 26 which is part of the IOL assembly 22 and extends radially outwardly from the circumference of the lens portion 24 of the IOL 22. The tab 26 extends outwardly along a plane of the IOL lens 24, or a parallel plane, and preferably also extends in the radially outward direction to a distance that is less that the distance that the haptic 28 extends in its plane, which is also preferably in a plane of the IOL lens, or a parallel plane. The outward extent of the haptic 28 is long enough to impinge on the capsular bag when the system is implanted, while the radially outward extent of the drug delivery device 30, when installed on the implanted IOL, is preferably shorter than that of the haptic, so as to avoid impingement of the drug delivery device on the capsular bag in the equatorial region of the capsular bag. The tab 26 shown in FIG. 3A includes a first radial portion 60, extending radially outwardly from a radially inward location (in this case, the circumferential edge of the IOL) which spans a first, small arc 61 along the circumferential edge of the IOL and also includes a second radial portion 62, extending from the first radial portion further radially outwardly and spanning a second arc 63 relative to the circumferential edge of the IOL lens which is larger than the first, small arc 61 of the first radial portion.

The corresponding drug delivery device shown in FIG. 3B includes a fixation portion 64 with a slot 65, extending from its radially inner surface 66, radially outwardly into the device and trough to the radially outer surface 67 (opposite the inner surface 66). The slot is configured relative to the tab to receive the tab, such that the second radial portion 62 may be resiliently compressed to a first configuration for passage through the slot, until the second radial portion 62 of the tab extends outwardly from the slot, and resiliently returns toward the second configuration which is wider than the slot, so that the tab, in conjunction with the slot, functions to secure the drug delivery device to the IOL assembly. (Conversely, the fixation portion (64) of the drug delivery device (30) may configured for resilient expansion to a first configuration to stretch over the second radial portion (62) of the tab (26) resilient return to return to a second configuration which is narrower than the second radial portion (62) of the tab (26).) The fixation portion may be configured as shown, or as a retaining ring extending posteriorly from drug delivery device, or as another form of anchor, fastener, or catch configured relative to the tab, to permit releasable attachment and detachment of the drug delivery device from the tab, without use of additional fastening elements or use of tools other than commonly used graspers and/or manipulating hooks. The system with a drug delivery device secured to the IOL assembly is shown FIG. 3C. FIG. 3D illustrates the system with first drug delivery devices disposed on each of two tabs.

The drug delivery device also comprises a therapeutic agent, which may comprise the entirety of the drug delivery device, or an anterior portion 68 of the drug delivery device (such as a pad) anterior to the fixation portion 64, or may be embedded within a drug eluting matrix which may also comprise the entirety of the drug delivery device, or an anterior portion of the drug delivery device (such as a pad).

The ocular implant system may be introduced into the eye of a patient, through a small incision at the edge of the cornea, and into the capsular bag of the patient. For initial installation of the drug delivery device, the drug delivery device may be fixed to the IOL assembly prior to insertion of both into the eye, and the assembled system may be folded and passed through the incision and then released in the capsular bag. For initial installation of the drug delivery device, the drug delivery device may be fixed to the IOL assembly after insertion of the IOL into the eye, by first inserting the IOL through the incision and releasing it in the capsular bag, and then inserting the drug delivery device through the incision and manipulating the drug delivery device to slip the fixation portion over the tab and thereby fix the drug delivery device to the tab and IOL assembly. When an originally implanted first drug delivery device is depleted, either by elution or bio-erosion, a subsequent surgical procedure may be performed in which a surgeon removes the original first drug delivery device, making another incision at the border of the cornea to insert and fix a new first drug delivery device to the tab and IOL assembly using a grasping tool. The removal of the original first drug delivery device and replacement with a new first drug delivery device may be performed, for example, after the original first drug delivery device is exhausted or depleted, or whenever it is desired to replace the original first drug delivery device with a new first drug delivery device which contains a different therapeutic agent, and may be performed after the incision made to implant the first drug delivery device has healed, and thus requires making a new incision. During the surgical procedure, if necessary, the surgeon may insert a grasping tool to remove the first drug delivery device from the tab and IOL assembly, and remove it from the eye, and insert a new drug delivery device and use the grasping tool to manipulate the new drug delivery device to slip it over the tab and thereby secure it to the IOL assembly.

In the embodiment shown in the FIGS. 4A through 4E, the ophthalmic implant 20 includes the IOL assembly, which includes a lens 24, a tab 26 and a haptic 28, and a secondary device 30. The ophthalmic implant 20 is characterized by an anterior surface 20A and a posterior surface 20P. In other embodiments the ophthalmic implant 20 may comprise other devices such as a capsular tension ring, or a capsular scaffold for holding the secondary device in place.

The secondary device 30 is a drug delivery device configured, as in FIGS. 3A through 3D, for attachment (preferably releasable attachment) to a tab 26 which is part of the IOL assembly 22 extends radially outwardly from the circumference of the lens portion 24 of the IOL 22. The tab extends outwardly along a plane of the IOL lens 24, or a parallel plane, and preferably also extends in the anterior direction to a distance that is less that the distance that the haptic 28 extends in it plane, which is also preferably in a plane of the IOL lens 24, or a parallel plane. The outward extent of the haptic is long enough to impinge on the capsular bag when the system is implanted, while the radially outward extent of the drug delivery device, when installed on the implanted IOL, is shorter than that of the haptic, so as to avoid impingement of the drug delivery device on the capsular bag in the equatorial region of the capsular bag. The tab 26 shown in FIG. 4B includes a first radial portion 60, extending radially outwardly from a radially inward location (in this case, the circumferential edge of the IOL) which spans a first, small arc 61 along the circumferential edge of the IOL and also includes a second radial portion 62, extending from the first radial portion further radially outwardly and spanning a second arc 63 relative to the circumferential edge of the IOL which is larger than the first, small arc 61 of the first radial portion.

Figure 4A:
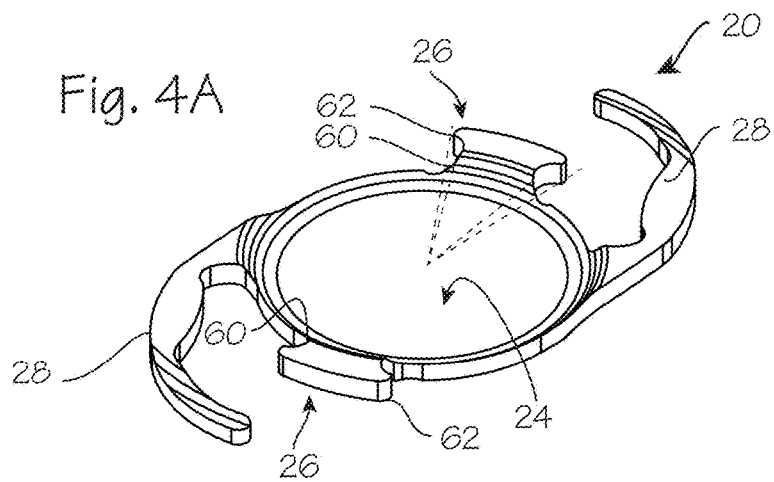
FIGS. 4A through 4E illustrate an ophthalmic implant system including an IOL assembly, a first drug delivery device and a second drug delivery device.
Figure 4B:
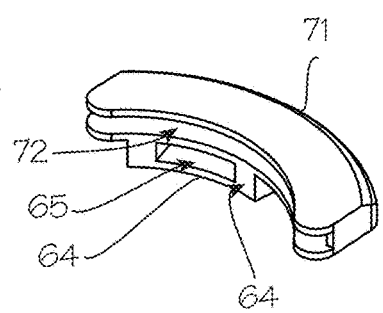

The corresponding drug delivery device shown in FIG. 4B includes a fixation portion 64 with a slot 65, extending from its radially inner surface 66, radially outwardly into the device, and, preferably, through to the radially outer surface 67. The slot is configured relative to the tab to receive the tab, such that the second radial portion 62 may be compressed to a first configuration for passage through the slot, until the second radial portion 62 of the tab extends outwardly from the slot, and resiliently returns toward the second configuration which is wider than the slot, so that the tab, in conjunction with the slot, functions to secure the drug delivery device to the IOL assembly. (Conversely, the fixation portion (64) of the drug delivery device (30) may configured for resilient expansion to a first configuration to stretch over the second radial portion (62) of the tab (26) and resiliently return to return to a second configuration which is narrower than the second radial portion (62) of the tab (26).) The fixation portion may be configured as shown, or as a retaining ring extending posteriorly from drug delivery device, or as another form of anchor, fastener, or catch configured relative to the tab, to permit releasable attachment and detachment of the drug delivery device from the tab, without use of additional fastening elements or use of tools other than commonly used graspers and/or manipulating hooks. The system with a drug delivery device secured to the IOL assembly is shown FIG. 4D. FIG. 4E illustrates the system with first drug delivery devices disposed on each of two tabs.

Figure 4C:
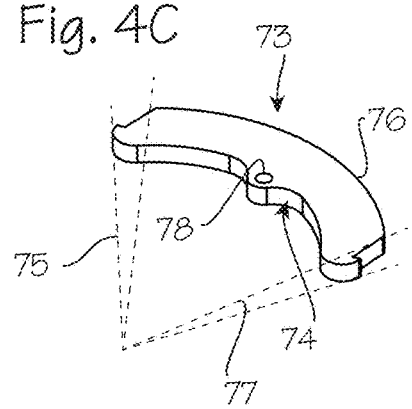

The drug delivery device 71 of FIG. 4B also comprises a compartment 72, with an opening on the radial inner surface (preferably), configured to fit a third device 73 shown in FIG. 4C. The third device is a second drug delivery device, and comprises a therapeutic agent, which may comprise the entirety of the second drug delivery device. The second drug delivery device may also comprise a drug eluting matrix with the therapeutic agent embedded within a drug eluting matrix which may also comprise the entirety of the second drug delivery device.

Figure 4D:
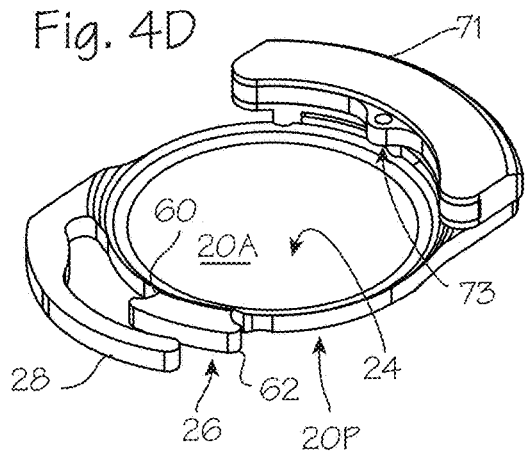
Figure 4E:
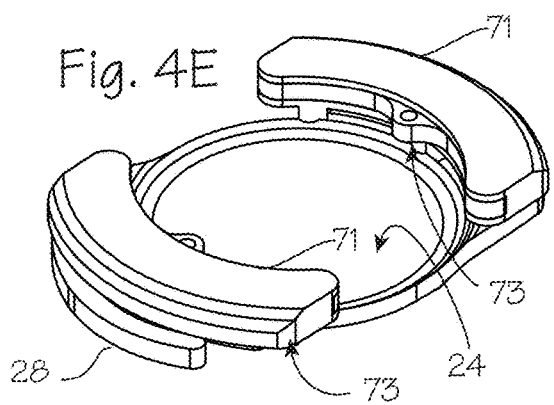

FIG. 4C illustrates a second drug delivery device 73 suitable for use with the first drug delivery device shown in FIG. 4B. As shown, the second drug delivery device may be formed as a drug pad configured, relative to the compartment 72 of the first drug delivery device, for a friction fit in the compartment, or other releasable attachment means (slight detents on one component and detent recesses on the other, for example) suitable for intraocular use. In the example shown in FIGS. 4A through 4E, the second drug delivery device may have an inner edge 74 subtending a first arc 75 and an outer edge 76 subtending a second arc 77 smaller than the first arc, and the compartment 72 has a corresponding opening approximating the first arc which narrows to the spacing approximating the second arc, to provide a friction fit for the second drug delivery device while allowing easy insertion of the second drug delivery device into the compartment. The second drug delivery device is provide with a pin-hole 78 proximate its inner edge, which is sized to accommodate a tool suitable for engagement with the pinhole (an ophthalmic hook may be used), with which the second drug delivery device can be manipulated for extraction of a second drug delivery device from the compartment, and insertion of a second drug delivery device into the compartment. With this arrangement, the second drug delivery device may be inserted into the compartment before implantation of the IOL, immediately after insertion of the IOL in an intra-operative time frame (that is, during the course of a same surgical operation in which the IOL is inserted), inserting the second drug delivery device into the eye after the IOL and first drug delivery device are implanted and then inserting the second drug delivery device into the compartment. Also, long after the surgical operation in which the IOL is inserted, the second drug delivery device may be removed in a second surgical operation and, optionally, replaced with a new second drug delivery device, for example, when a drug eluting second drug delivery device has eluted much of the therapeutic agent which was initially embedded in the second drug delivery device. The assembled ophthalmic implant, including the IOL assembly, first drug delivery device and second drug delivery device, is illustrated in FIG. 4D. FIG. 4E illustrates the system with first and second drug delivery devices disposed on each of two tabs.

The ocular implant system of FIGS. 4A through 4E may be introduced into the eye of a patient, through a small incision at the edge of the cornea, and into the capsular bag of the patient. For initial installation of the drug delivery device, the drug delivery device may be fixed to the IOL assembly prior to insertion of both into the eye, and the assembled system may be folded and passed through the incision and then released in the capsular bag. Likewise, the second drug delivery device (the drug pad) can be secured within the first drug delivery device before or after prior to insertion of both into the eye. For initial installation of the drug delivery device, the second drug delivery device may be fixed to the first drug delivery device after insertion of the first drug delivery device into the eye, by first inserting the first drug delivery device through the incision and releasing it in the capsular bag, and then inserting the second drug delivery device through the incision and manipulating the second drug delivery device to insert it into the compartment 72 of the first drug delivery device. When a second drug delivery device is depleted, either by elution or bio-erosion, a subsequent surgical procedure may be performed in which a surgeon removed the original second drug delivery device, making another incision at the border of the cornea to insert and fix a new second drug delivery device within the compartment 72 using a grasping tool. If necessary, the surgeon may insert a grasping tool to remove the original second drug delivery device from the compartment of the first drug delivery device, and remove it from the eye, and insert a new second drug delivery device and use the grasping tool to manipulate the new second drug delivery device to slip it into the compartment and thereby secure it to the first drug delivery device.

In each embodiment described above, the drug delivery device of FIGS. 3A through 3D or the second drug delivery device (the drug pad) of FIGS. 4A through 4E can be configured to deliver various therapeutic agents to treat various conditions. Brimonidine, latanoprost, timolol, pilocarpine, brinzolamide and other drugs in the general categories of beta blockers, alpha agonists, ROCK Inhibitors, adenosine receptor agonists, carbonic anhydrase inhibitors, adrenergic and cholinergic receptor activating agents, and prostaglandin analogues may be incorporated into the drug delivery devices to treat glaucoma. Aflibercept, bevacizumab, pegaptanib, ranibizumab, steroids, and aptamers may be incorporated into the drug delivery devices to treat wet macular degeneration. Complement factors, anti-oxidants and anti-inflammatory agents may be incorporated into the drug delivery devices to treat dry macular degeneration. Methotrexate, antibodies, dexamethasone, triamcinolone, and other steroid agents may be incorporated into the drug delivery devices to treat uveitis. Anti-proliferative agents, anti-mitotic agents, anti-inflammatory agents, and other medications that would inhibit the spread of lens epithelial cells may be incorporated into the drug delivery devices to treat posterior capsular opacification. Antibiotics such as fluoroquinolones, non-steroidal agents such as ketorolacs, and steroids such as prednisolones may be incorporated into the drug delivery devices for post-op management after cataract surgery include.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

What is claimed is:

1. A method of implanting an ophthalmic implant, the method comprising:
   providing an ophthalmic implant comprising:
   an IOL assembly and a drug delivery device;
   said IOL assembly comprising a lens, a tab, and a haptic, said IOL assembly characterized by an anterior surface and a posterior surface, said IOL assembly configured for implantation into an eye of a patient with said anterior surface disposed anterior to said posterior surface;
   said tab extending from the lens, said tab configured for engaging the drug delivery device, said haptic extending in a plane of the lens, radially outwardly from the lens, such that said haptic is configured to hold the IOL assembly in place within a capsular bag of the eye of the patient;
   said drug delivery device comprises a first compartment, said first compartment having a first aperture sized and dimensioned to receive the tab and secure the drug delivery device to the IOL assembly;
   said drug delivery device having an arcuate form, characterized by an inner curve and an outer curve, wherein the first aperture is disposed on the inner curve;
   the drug delivery device further comprises a drug pad comprising a matrix with a therapeutic agent embedded or dispersed within the matrix;
   injecting the IOL assembly and drug delivery device into the eye of the patient;
   joining the drug delivery device to the IOL assembly by fitting a fixation portion of the drug delivery device onto the tab of the IOL assembly; and
   positioning the joined drug delivery device and IOL assembly in the eye of the patient with the IOL assembly held in place by a capsular bag of the eye of the patient.

2. The method of claim 1, wherein the step of joining the drug delivery device to the IOL assembly is performed before the step of injecting the IOL assembly and drug delivery device into the eye of the patient.

3. The method of claim 1, wherein the step of joining the drug delivery device to the IOL assembly is performed after the step of injecting the IOL assembly and drug delivery device into the eye of the patient.

4. The method of claim 1, further comprising the step of:
   after injecting the IOL assembly and drug delivery device into the eye of the patient, removing the drug delivery device from the eye of the patient without removing the IOL assembly from the eye of the patient, and inserting a new drug delivery device into the eye of the patient, and joining the new drug delivery device to the IOL assembly by fitting a fixation portion of the new drug delivery device onto the tab of the IOL assembly.

5. The method of claim 1, wherein:
   the step of injecting the IOL assembly and drug delivery device into the eye of the patient is accomplished by creating a first incision in the eye of the patient proximate an edge of a cornea of the eye of the patient; and
   the method further comprises the step of:
   after injecting the IOL assembly and drug delivery device into the eye of the patient, and after the first incision has healed, creating a new incision in the eye of the patient for removing the drug delivery device from the eye of the patient through the new incision without removing the IOL assembly from the eye of the patient, and inserting a new drug delivery device into the eye of the patient through the new incision, and joining the new drug delivery device to the IOL assembly by fitting a fixation portion of the new drug delivery device onto the tab of the IOL assembly.

6. The method of claim 1, wherein:
   the step of injecting the IOL assembly and drug delivery device into the eye of the patient is accomplished by creating a first incision in the eye of the patient proximate an edge of a cornea of the eye of the patient; and
   the method further comprises the step of:
   after injecting the IOL assembly and drug delivery device into the eye of the patient, and after drugs in the drug delivery device are depleted, creating a new incision in the eye of the patient for removing the drug delivery device from the eye of the patient through the new incision without removing the IOL assembly from the eye of the patient, and inserting a new drug delivery device into the eye of the patient through the new incision, and joining the new drug delivery device to the IOL assembly by fitting a fixation portion of the new drug delivery device onto the tab of the IOL assembly.

7. A method of implanting an ophthalmic implant, the method comprising:
   providing an ophthalmic implant comprising an IOL assembly, a drug delivery device, and a drug pad;
   said IOL assembly comprising a lens, a tab, and a haptic, said IOL assembly characterized by an anterior surface and a posterior surface;
   said tab extending from the lens, said tab configured for engaging the drug delivery device, said haptic extending in a plane of the lens, radially outwardly from the lens, such that said haptic is configured to hold the IOL assembly in place with a capsular bag of a eye of the patient;
   said drug delivery device comprises a fixation portion having a first compartment, and said drug delivery device having a second compartment, said first compartment having a first aperture sized and dimensioned to receive the tab and secure the drug delivery device to the IOL assembly, said second compartment having a second aperture sized and dimensioned to receive the drug pad;
   said drug delivery device having an arcuate form, characterized by an inner curve and an outer curve, wherein the first aperture and second aperture are disposed on the inner curve;
   injecting the IOL assembly, drug delivery device, and drug pad into the eye of the patient;
   joining the drug delivery device to the IOL assembly by fitting the fixation portion of the drug delivery device onto the tab of the IOL assembly; and
   inserting the drug pad into the second compartment; and
   positioning the joined drug pad, drug delivery device, and IOL assembly in the eye of the patient with the IOL assembly held in place by a capsular bag of the eye of the patient.

8. The method of claim 7, wherein the step of joining the drug delivery device to the IOL assembly is performed before the step of injecting the IOL assembly and drug delivery device into the eye of the patient.

9. The method of claim 7, wherein the step of joining the drug delivery device to the IOL assembly is performed after the step of injecting the IOL assembly and drug delivery device into the eye of the patient.

10. The method of claim 7, wherein the step of inserting the drug pad into the second compartment of the drug delivery device is performed before the step of injecting the IOL assembly and drug delivery device into the eye of the patient.

11. The method of claim 7, wherein the step of inserting the drug pad into the second compartment of the drug delivery device is performed after the step of injecting the IOL assembly and drug delivery device into the eye of the patient.

12. The method of claim 7, further comprising the step of:
after injecting the IOL assembly, drug delivery device, and drug pad into the eye of the patient, removing the drug pad from the eye of the patient without removing the IOL assembly and drug delivery device from the eye of the patient, and inserting a new drug pad into the eye of the patient, and inserting the new drug pad into the second compartment of the drug delivery device.

13. The method of claim 7, wherein:
the step of injecting the IOL assembly, drug delivery device, and drug pad into the eye of the patient is accomplished by creating a first incision in the eye of the patient proximate an edge of a cornea of the eye of the patient; and
the method further comprises the step of:
after injecting the IOL assembly, drug delivery device, and drug pad into the eye of the patient, and after the first incision has healed, creating a new incision in the eye of the patient for removing the drug pad from the eye of the patient through the new incision without removing the IOL assembly and drug delivery device from the eye of the patient, and inserting a new drug pad into the eye of the patient through the new incision, and inserting the new drug pad into the second compartment of the drug delivery device.

14. The method of claim 7, wherein:
the step of injecting the IOL assembly, drug delivery device, and drug pad into the eye of the patient is accomplished by creating a first incision in the eye of the patient proximate an edge of a cornea of the eye of the patient; and
the method further comprises the step of:
after injecting the IOL assembly, drug delivery device, and drug pad into the eye of the patient, and after the drug pad is depleted, creating a new incision in the eye of the patient for removing the drug pad from the eye of the patient through the new incision without removing the IOL assembly and drug delivery device from the eye of the patient, and inserting a new drug pad into the eye of the patient through the new incision, and inserting the new drug pad into the second compartment of the drug delivery device.

* * * * *